United States Patent [19]

Thow

[11] 4,057,065

[45] Nov. 8, 1977

[54] PERCUTANEOUS GASTROINTESTINAL TUBE

[75] Inventor: G. Bruce Thow, Champaign, Ill.

[73] Assignee: Dow Corning Corporation, Midland, Mich.

[21] Appl. No.: 698,397

[22] Filed: June 21, 1976

[51] Int. Cl.² .......................................... A61M 25/00
[52] U.S. Cl. ............................... 128/348; 128/349 B
[58] Field of Search ............................... 128/348–351, 128/276–278

[56] References Cited

U.S. PATENT DOCUMENTS

| | | | |
|---|---|---|---|
| 2,230,218 | 2/1941 | Asche | 128/276 |
| 2,498,692 | 2/1950 | Mains | 128/348 X |
| 2,854,982 | 10/1958 | Pagano | 128/348 |
| 2,930,377 | 3/1960 | Cowley | 128/349 B |
| 3,144,868 | 8/1964 | Jascalevich | 128/349 B |

OTHER PUBLICATIONS

Grosfeld et al., Arch. Surg., vol. 110, May 1975, pp. 594–599.

Primary Examiner—Dalton L. Truluck
Attorney, Agent, or Firm—Jack I. Pulley

[57] ABSTRACT

In accordance with a preferred embodiment of this invention, there is provided a percutaneous gastrointestinal tube which may be surgically inserted into the patient's stomach and then threaded downward into the intestine to provide body intestinal stent plication, and independently controllable gastric and/or intestinal decompression. The subject gastrointestinal tube preferably has two decompression lumens and two inflatable cuffs. One decompression lumen extends the full length of the tube and is vented at the distal end to provide decompression to the lower portion of the intestine, the other decompression lumen is vented so as to decompress the stomach. One inflatable cuff is located near the distal end to facilitate the threading of the tube into the small intestine, and the other inflatable cuff is positioned in the stomach at the inner surface of the incision to help seal the incision and to prevent the inadvertent partial withdrawal of the subject tube.

1 Claim, 6 Drawing Figures

PERCUTANEOUS GASTROINTESTINAL TUBE

This invention relates to gastraintestinal tubes.

The effective control of adhesions is necessary to any surgical procedure which may disrupt the intestine. After such surgery it is very difficult, if not impossible, to prevent the formation of adhesions (i.e., new adhesive fixations) around the intestine; however, failure to control this formation may lead to serious post-operative complications such as intestinal obstructions caused by the adhesions forming around sharp curves in the intestine and crimping the intestinal lumen. In most cases, this type of complication requires additional surgery, and this, in turn, may generate the formation of more adhesions and further complicate the patient's condition.

To prevent this type of adhesion related problem, the surgeon may insert a flexible tube into the intestine to ensure that it will lie in gentle, obstruction free curves as the adhesions form during healing. This procedure is termed intestinal stent plication and has been described in articles such as "Long Tube Gastrostomy With Internal Intestinal Splinting in Inflammatory Disease of the Small Intestine," by G. Bruce Thow, M.D., *Diseases of the Colon and Rectum*, Vol. 15, No. 1, January-February, 1972, published by J. P. Lippincott Company, U.S.A.

Typically, these tubes are either surgically inserted or threaded downward through the nasal passage through the stomach and into the intestine. The former method is preferred because of the extreme discomfort associated with the nasal-gastric technique. In the use of intestinal tubes several problems arise. For example, it is often necessary to withdraw fluids from (i.e., to decompress) both the stomach and the intestine both during and after surgery. In addition, it is often times desirable to decompress the stomach and the intestine independently with a high degree of control over each. This is difficult with typical prior art intestinal tubes which either alternatively provide means to decompress the stomach or the intestine or provide a single lumen that is vented into both the stomach and the intestine.

In addition, percutaneous tubes must be held in position; the incision must be closed, and a good seal formed between the tube and the flesh during the 5 to 20 day period that the tube may remain in the patient's body. An effective seal is needed to prevent bacteria from entering the wound and gastric fluids from leaking. The importance of an effective seal at this point becomes apparent when one realizes the high risk of infection and tissue damage due to contact with digestive fluids associated with any gastric incision which must remain open for an extended period of time. These risks are compounded if there is any significant internal leakage from the stomach into the abdominal cavity. In addition, if the tube is partially withdrawn, it is difficult, if not impossible, to reposition the tube and probability of the aforementioned adhesion related problems is significantly increased. In the past, these problems have been managed wih the combination of a purse string suture to seal the incision around the tube and a retention suture to hold the tube in position; this is at best a "make do" technique.

This invention provides a percutaneous gastrointestinal tube specifically designed to be inserted through a gastrostomy and easily threaded downward into the small intestine to provide both intestinal stent plication and effective and independently controllable, gastric and or intestinal decompression.

This invention also provides a percutaneous gastrointestinal tube which greatly reduces the danger of infection by helping to effectively seal the incision, and which also greatly reduces the possibility of the inadvertent partial withdrawal of the tube.

The subject gastrointestinal tube comprises a flexible elongated elastomeric member having two decompression lumens and two inflatable cuffs. One decompression lumen extends from the proximal end (that end which remains outside the patient's body) of the subject gastrointestinal tube through the entire length of the subject tube and is vented at or near the distal end (opposite to proximal) to provide decompression to the lower sections of the intestine. The other decompression lumen extends from the proximal end into the stomach and is vented there to provide gastric decompression. One inflatable cuff is located at or near the distal end of the subject tube and is preferably inflated as the surgeon inserts the subject tube to facilitate the threading of the distal end of the subject tube downward from the stomach into the intestine. The upper inflatable cuff is positioned on the tube so that, once the tube is in place, this cuff will be in the stomach at the inner surface of the incision to help seal the incision and to prevent the inadvertent partial withdrawal of the tube. Preferably, the subject tube also has two independently controllable inflation-deflation lumens, with one extending from the proximal end of the subject tube to each inflatable cuff. In addition, the subject gastrointestinal tube preferably has a molded end portion securely attached to the proximal end of the subject tube to provide ready access to and independent control over each lumen. Any or all of the lumens in the subject tube may be equipped with a control valve which would preferably be located in the molded end portion.

These and other features, objects and advantages of the subject invention will be more readily understood in view of the following detailed description which will make reference to the attached drawings which are:

Figure 1:
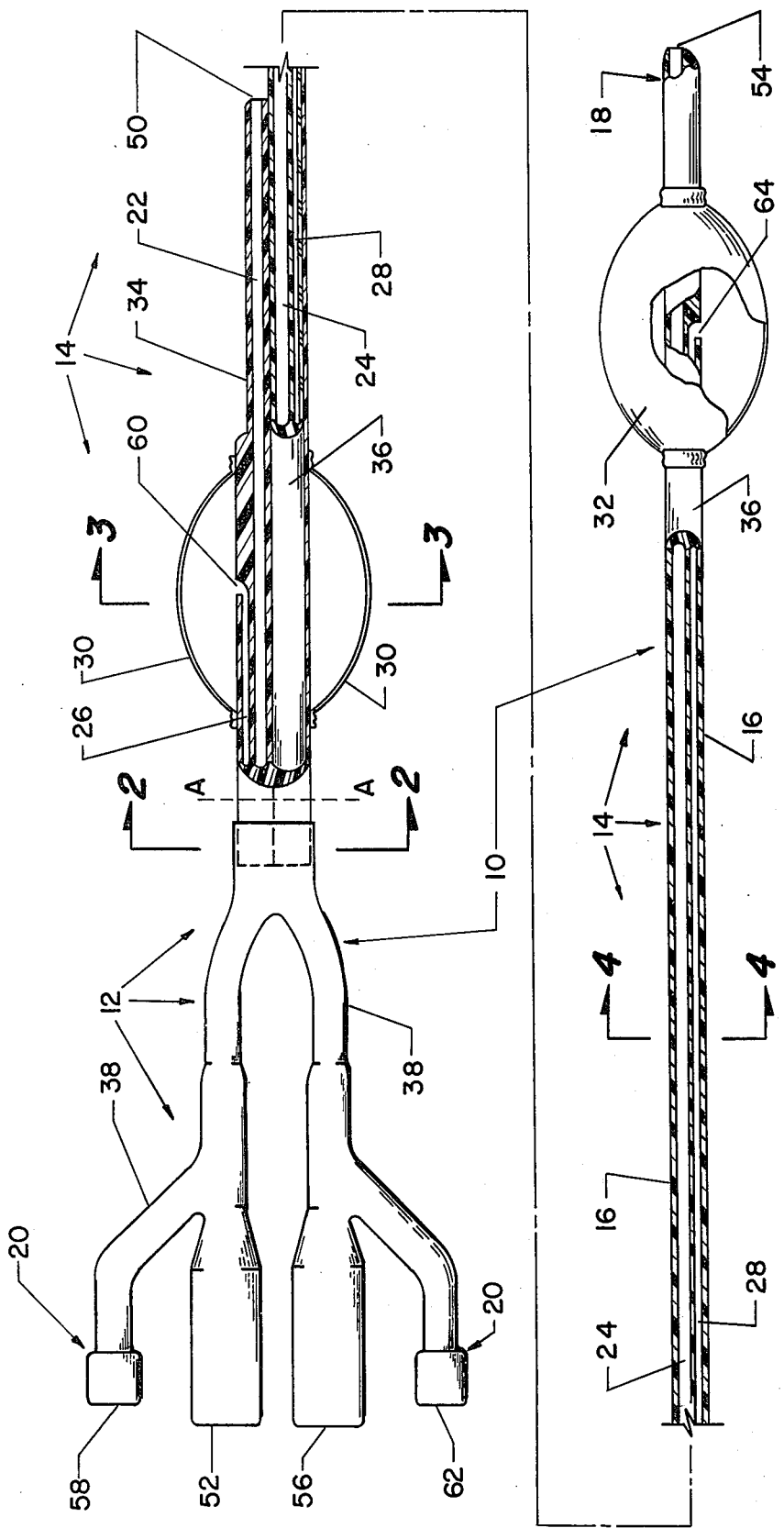
FIG. 1 is an elevated cut-away view of one preferred embodiment of the subject percutaneous gastrointestinal tube with both cuffs inflated.

In accordance with a first preferred and illustrative embodiment, as shown in FIG. 1, the subject percutaneous gastrointestinal tube 10 comprises an elongated, smooth surfaced, member 16 formed of a soft flexible elastomer and an end piece 38. The subject tube 10 should be able to withstand a thorough cleaning and sterilization and also should be compatible with, that is cause no significant irritation to, human body tissue after contact therewith for a period of up to several weeks or more. This compatibility may be provided by either forming the subject tube 10 from a base elastomer which is, itself, compatible with the human body or coating a tube with a compatible material. Suitable elastomeric materials which may be compatible with the human body, if the formulations are controlled so as to avoid harmful additives, include vulcanized gum rubber, silicone rubber, butyl rubber, natural rubber, butadienestyrene copolymers, and the like. However, the particular base elastomer is not critical to the subject invention and the above are included as merely illustrative and not limiting examples.

With reference to the aforementioned coating technique, the subject tube 10 may be formed of a silicone rubber coated elastomer such as that described and fully disclosed in U.S. Pat. No. 3,434,869. This patent is hereby incorporated by reference to illustrate that particular silicone rubber coated elastomeric structure.

The subject tube 10 may be viewed as having two portions; an upper proximal portion 12, in FIG. 1, which remains external to the patient's body during use and a lower distal portion 14 which is inside the patient's body once the subject tube 10 is in place. Line A—A indicates the approximate position on the subject tube 10 of the incision when the subject tube 10 is properly placed in the patient's body and therefore represents the dividing line between the proximal portion 12 and the distal portion 14. Preferably, both the proximal portion 12 and the distal portion 14 of the subject tube 10 will have an outside diameter of about one quarter of an inch. However, the exact dimensions of the subject tube 10 are not critical to this invention, as long as the distal portion 14 will readily fit inside the intestinal lumen.

During any surgical procedure which indicates either intestinal stent plication, or decompression of the stomach and or the intestine, or both, the distal portion 14 of the subject tube 10 may, after being suitably cleaned and sterilized, be surgically inserted into the patient's stomach 40 (See FIG. 5) and then threaded downward into the intestine 44. The presence of the elongated elatomeric distal portion 14 of the subject tube 10 will ensure that the intestine 44 will remain in a gently curving configuration during the healing process. Therefore, as the patient recovers any adhesions, that may form, will not obstruct or crimp the intestinal lumen because there will be no sharp curves or kinks in the intestine 44. In addition, it is to be noted that the subject tube 10 may be extended to plicate and/: or decompress the colon 48.

To provide either or both gastric and intestinal decompression, the subject tube 10 has two decompression lumens; a stomach decompression lumen 22 (See FIGS. 1, 2, and 3) which extends through the proximal portion 12 and the upper portion of the distal portion 14 and is vented in the stomach 40 (See FIG. 5) and an intestinal decompression lumen 24 (See FIGS. 1, 2, 3 and 4) which extends the entire length of the subject tube 10 and is vented at or near the distal end 18. More specifically, the stomach decompression lumen 22 provides independently controllable fluid communication between a distal stomach decompression lumen opening 50 which will be in the patient's stomach 40 when the subject tube 10 is in place, and a proximal stomach decompression lumen opening 52 in the proximal end 20 of the subject tube 10. This communication provides a means to withdraw or insert either or both liquids and gases from the patient's stomach to relieve stress on the stomach 40 and ensure that no undue pressure will be placed on the stomach wall 42 (See FIG. 5). This is particularly important if an incision has been made in the stomach wall 42 since such pressure may post-operatively rupture or re-open this incision. In addition, by removing the excess gases and liquids from the stomach 40, they are not passed through to stress the distal gastrointestinal tract.

Similarly, the intestinal decompression lumen 24 provides fluid communication between a distal intestinal decompression lumen opening 54 in the distal end 18 of the subject tube 10 and a proximal intestinal decompression lumen opening 56 in the proximal end 20 of the subject tube 10. The intestinal lumen 24 is primarily used to withdraw liquids and gases, that is to decompress, the patient's intestine 44 and/or colon 48. This intestinal decompression procedure is particularly useful as the surgeon is threading the subject tube 10 downward from the patient's stomach 40 into the intestine 44 since the slightly lower pressure ahead of the distal end 18 helps to pull the tube 10 through the intestinal lumen.

Figures 2, 3, 4:
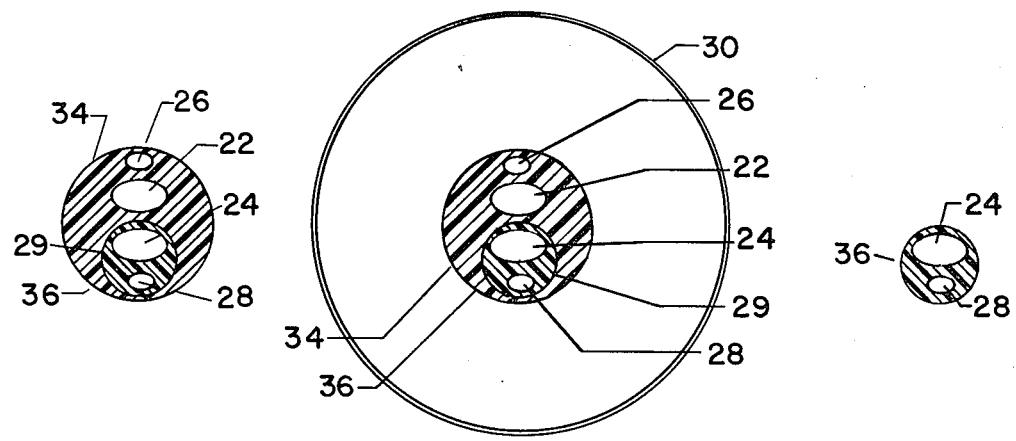
FIG. 2 is a cross-sectional view of the subject percutaneous gastrointestinal tube taken at section 2—2 of FIG. 1.
FIG. 3 is a cross-sectional view of the subject percutaneous gastrointestinal tube taken at section 3—3 of FIG. 1.
FIG. 4 is a cross-sectional view of the subject percutaneous gastrointestinal tube taken at section 4—4 of FIG. 1.

As shown in FIGS. 2, 3 and 4 the decompression lumens have an oval shape and are about one hundred mils wide. However, it is to be understood that the exact size and shape of the lumens, to include both the decompression and the inflation-deflation lumens, is not critical to the practice of this invention. The size and shape of all lumens may, within limits, be dictated by processing or material factors; the primary limit is that the size and shape should be adequate to provide the desired fluid communication. A danger to be noted is that as the size of the lumens decrease, the lumens may be crimped and thereby closed by the curves which the subject tube 10 will assume in the patient's body.

A particular advantage of the subject tube 10 is that there are separate and independently controllable means to decompress the stomach 40 and the intestine 44. This provides the surgeon with an extra degree of freedom to provide specific and readily controllable relief measures when and where necessary. This is a significant improvement over prior art gastrointestinal tubes having one lumen which is vented in both the stomach 40 and the intestine 44 or colon 48. Such prior art tubes do not provide the surgeon with adequate control of either the gastric or intestinal decompression procedures and there are often problems with leakage and in providing adequate decompression to either or both areas.

Examples of situations where the independence between the stomach decompression lumen 22 and the intestinal decompression lumen 24, are very important include where it is necessary to decompress or drain the lower intestinal tract and where a portion of the intestinal decompression lumen becomes plugged.

In the former case, which would include procedures such as an intestinal anastomosis (i.e., where a segment of the intestine is removed and the two ends rejoined) it is very important to drain any fluids from that region where the intestine has been rejoined. If this region is not effectively drained and there is leakage, the complications may be severe. However, if the lumen, which decompresses the anastomosis region, is also vented in the stomach, there will be some leakage of the fluids from the anastomosis region into the stomach 40. This is not an acceptable condition.

In the later case, where the intestinal decompression lumen becomes plugged, it is not possible to apply either a positive or negative pressure to the lumen or even to flush the lumen without disrupting the stomach, because the decompression lumen is also vented in the stomach. These two situations clearly and effectively demonstrate some of the advantages of the subject gastrointestinal tube.

The distal portion 14 of the subject tube 10 is provided with two, fixed and thin walled, inflatable cuffs, an upper inflatable cuff 30 and a lower inflatable cuff 32. The upper inflatable cuff 30 is positioned near the proximal portion 12, and is typically inflated after the subject device has been inserted and positioned in the patient's body. After the upper inflatable cuff 30 is inflated, it is positioned against the inner surface of the stomach wall 42 at the incision and serves several purposes during the extended period of time the device may remain within the patient's body. First, the upper inflatable cuff 30 positions the subject tube 10 and prevents the inadvertent partial withdrawal of the subject tube 10. This is important since the subject device will remain in position for up to two weeks or more until the healing process has progressed to a point where the adhesions have developed adequately to sustain the intestines in an obstruction free configuration. Secondly, the upper inflatable cuff 30 helps in sealing the incision and preventing any leakage of intestinal fluids into the abdominal cavity which could easily lead to peritonitis and/or other complications.

The lower inflatable cuff 32 is positioned near the distal end 18 of the subject tube 10 and is preferably inflated after the distal end 18 of the subject tube 10 and the lower inflatable cuff 32 have been inserted through the stomach 40 and passed through the pyloris, jejunum, and the ligament of Trietz. Once the lower inflatable cuff 32 is inflated, typically with water to provide a firm balloon, the surgeon is able to manually control the distal end 18 of the subject tube 10 through the intestinal wall 46 and quickly thread it downward as far as necessary.

An upper cuff inflation-deflation lumen 26 provides fluid communication between a proximal upper cuff lumen opening 58 in the proximal end 20 of the subject tube 10 and the upper inflatable cuff 30 through an internal upper cuff lumen opening 60. Similarly, a lower cuff inflation-deflation lumen 28 provides fluid communication between a proximal lower cuff lumen opening 62 in the proximal end 20 of the subject tube 10, and the lower inflatable cuff 32 through an internal lower cuff lumen opening 64. It is through these inflation-deflation lumens 26 and 28, that the surgeon may independently inflate and deflate the cuffs 30 and 32. Preferably, these are valves (not shown) located in the proximal end 20 in each cuff lumen to provide a means of controlling the flow of fluids through them. If desired, valves may be included in the other lumens as well. The term "controllable lumen" as used herein designates a lumen having a valve or other means to regulate the flow of fluids therein. The particular valve and its internal mechanism is not critical to the subject invention and any valve known in the art which could readily be attached to the subject tube 10 and adequately provide the necessary opening and sealing functions would be suitable.

Figure 5:
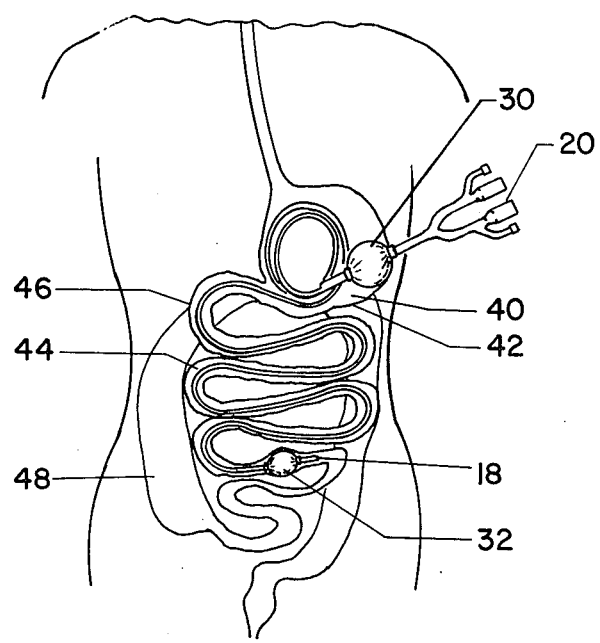
FIG. 5 is a representative view of a patient's stomach and intestines showing the subject percutaneous gastrointestinal tube in place.

The subject gastrointestinal tube may be formed by any of several different processes and combinations thereof including extrusion, molding and the like. Preferably, the subject tube 10 is formed from three basic components: (1) a sleeve portion 34 which is preferably an extrusion product; (2) an insert portion 36 which, also is preferably an extrusion product; and (3) an end piece 38, which is preferably a molded product. As clearly shown in FIGS. 1, 2 and 3 the sleeve portion 34 is relatively short when compared to the insert portion 36, and as shown in FIG. 5 extends through the incision and terminates in the patient's stomach. In addition, the sleeve portion 34 haa an elongated tubular shape and preferably a circular cross-section and contains the stomach decompression lumen 22 and the upper cuff inflation-deflation lumen 26 which vents into the upper inflatable cuff 30 through the internal upper cuff lumen opening 60. The sleeve portion 34 also carries the insert portion 36 (See FIGS. 2 and 3) in an insert carrying lumen 29. In turn, the insert portion 36 contains the intestinal decompression lumen 24 and the lower cuff inflation-deflation lumen 28 which vents into the lower inflatable cuff 32 through the internal lower cuff lumen opening 64. Typically the sleeve portion 34 and the insert portion 36 would be formed separately, by an extrusion or molding technique. As these two portions are separately formed, the inside dimensions of the insert carrying lumen 29 in the sleeve portion 34 and the outside dimensions of the insert portion 36 are controlled so that the former are slightly smaller than the latter. To form the assembly of the sleeve portion 34 and the insert portion 36, the sleeve portion 34 is immersed briefly in a suitable solvent to swell the sleeve portion 34 and more specially to increase the diameter of the insert carrying lumen 29. The insert portion 36 is then inserted into the insert carrying lumen 29 and the solvent is removed to form a solvent shrink fit.

The insert portion 36 also has an elongated tubular shape and forms a major portion of the distal portion 14 of the subject tube 10. The insert portion 36 contains the intestinal decompression lumen 24 and the lower cuff inflation-deflation lumen 28 through which the shape of the lower inflatable cuff 32 is controlled.

The end piece 38 is securely attached, preferably with a suitable adhesive, to proximal end 35 of the sleeve portion 34 and serves to separate the four lumens and provide easy access thereto. In addition, the end piece 38, may contain valves (not shown) for each of the lumens and/or connector means to facilitate the attachment of suction or pressure providing appliances to each of the lumens. Typically, the cuffs are formed separately and securely attached, by means of a suitable adhesive to assembled distal portion 14.

Figure 6:
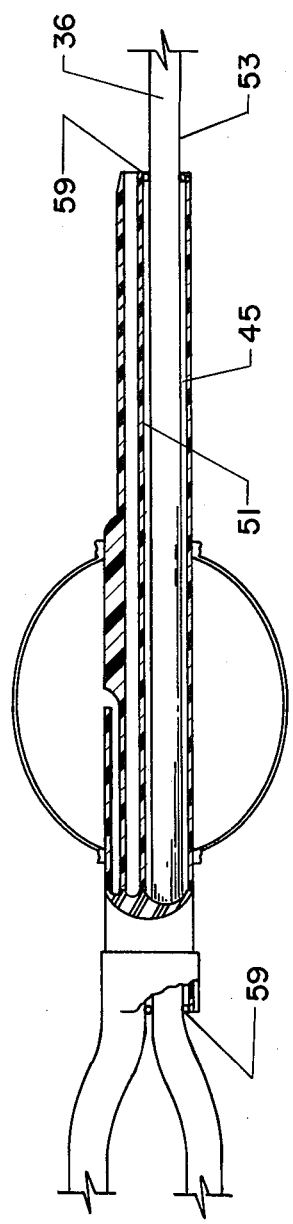
FIG. 6 is an elevated cut-away view of the upper cuff of a second preferred embodiment of the subject percutaneous gastrointestinal tube, this embodiment features a slidably attached upper inflatable cuff.

In accordance with a second preferred embodiment the solvent shrink fit, which securely attaches the sleeve portion 34 to the insert portion 36, is replaced with a lubricated slidable fit (See FIG. 6). By this technique, it is possible to slide the sleeve portion 34 along the insert portion 36, and this allows the surgeon to adjust the length of the distal portion 14 of the subject tube 10. Typically, the subject tube 10 is about 9 feet long and the distal portion 14 is about 8½ feet in length. However, it may not be desirable, in all cases, to have 8½ feet of tubing within the patient's body for an extended period of time, especially when the distal end 18 is not fully threaded into the intestine 44 and a significant portion is left coiled in the stomach 40.

To provide a slidable fit between the sleeve portion 34 and the insert portion 36, either the diameter of the insert carrying lumen 29 is increased or the outside diamter of the insert portion 36 is decreased or both. In addition, a lubricating fluid film 45 is provided between the inner surface 51 of the insert carrying lumen 29 and the outer surface 53 of the insert portion 36. A low to moderate viscosity silicone fluid would be a suitable lubricant. To prevent the lubricating fluid from leaking out, O-rings 59 would be used to seal each end of the insert carrying lumen 29.

As shown in FIG. 6, the insert portion 36 would extend completely through the sleeve portion 34 and two separate end pieces could be used to provide separate access to the individual lumens. One end piece 41 would fit onto that section of the insert portion 36 which would extend beyond the proximal end of the sleeve portion 34 and a second end piece 39 would fit onto an extension of the proximal end of the sleeve portion 34.

While my invention has been described in terms of certain specific embodiments, it will be appreciated that other forms thereof could readily be adopted by one skilled in the art. Therefore, the scope of my invention is not to be limited to the specific embodiments disclosed.

That which is claimed is:

1. A percutaneous gastrointestinal tube for providing intestinal stent plication and separate and independently controllable gastric and intestinal decompression, said tube comprising an elongated elastomeric member, having a distal portion which is surgically insertable through an incision into the patient's stomach and then threadable downward into the intestine and a proximal portion extending from said distal portion and remaining external to the patient's body when in use; said elastomeric member also having a. a stomach decompression lumen to provide fluid communication between a distal stomach decompression lumen opening in the section of the distal portion which will be in the patient's stomach when said tube is properly disposed in the patient's body, and a proximal stomach decompression lumen opening in said proximal end of said tube;

b. an intestinal decompression lumen to provide fluid communication between a distal intestinal decompression lumen opening disposed at or near the lower distal end of said member and a proximal intestinal decompression lumen opening in the proximal end of said tube;

c. an upper inflatable cuff means for retaining and positioning said member adjacent the inner surface of the stomach wall and to help seal the incision at the inner surface of the stomach;

d. an upper cuff inflation-deflation lumen to provide fluid communication between said upper inflatable cuff means and a proximal upper cuff opening disposed in said proximal portion of said tube;

e. a lower inflatable cuff means disposed near the lower distal end of said member, for insertion of said tube into the patient's body to facilitate the threading of said member downward from the stomach into the intestine, said lower cuff means being inflated during a part of the insertion of said tube into the patient's body; and f. a lower cuff inflation-deflation lumen connecting and providing fluid communication between said lower inflatable cuff means and a proximal lower cuff opening disposed in said proximal portion of said tube.

* * * * *

UNITED STATES PATENT AND TRADEMARK OFFICE
CERTIFICATE OF CORRECTION

PATENT NO. : 4,057,065
DATED : November 8, 1977
INVENTOR(S) : G. BRUCE THOW

It is certified that error appears in the above-identified patent and that said Letters Patent are hereby corrected as shown below:

In the Abstract, line 5, "body" should read --both--.

Column 1, line 58, after the word "and" insert --the--.

Column 1, line 61, "wih" should read --with--.

Column 5, line 33, Trietz" should read --Treitz--.

Column 5, line 50, "these" should read --there--.

Column 6, line 6, "haa" should read --has--.

Column 6, line 27, "specially" should read --specifically--.

Column 6, line 64, "diamter" should read --diameter--.

Signed and Sealed this

Eighteenth Day of November 1980

[SEAL]

Attest:

SIDNEY A. DIAMOND

Attesting Officer  Commissioner of Patents and Trademarks